(12) United States Patent
Pond et al.

(10) Patent No.: US 6,436,380 B1
(45) Date of Patent: *Aug. 20, 2002

(54) BALDNESS COSMETIC AND METHOD OF APPLICATION

(75) Inventors: Kenneth Pond, Brisbane (AU); Ronald M. Popeil, Las Vegas, NV (US); Alan L. Backus, Los Angeles, CA (US)

(73) Assignee: Advantage Partners LLC, La Canada, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/810,974

(22) Filed: Feb. 27, 1997

Related U.S. Application Data

(63) Continuation of application No. 08/432,497, filed on May 1, 1995, now abandoned, which is a continuation of application No. 07/999,740, filed on Dec. 31, 1992, now abandoned.

(51) Int. Cl.⁷ .......................... A61K 9/12; A61K 7/021; A61K 47/32
(52) U.S. Cl. .......................... 424/63; 424/47; 424/70.1; 424/DIG. 1; 424/78.03; 424/70.6; 514/772.5
(58) Field of Search .................. 424/47, 70.1, 70.6, 424/78.02, 78.03, DIG. 1, 63; 514/772.5

(56) References Cited

U.S. PATENT DOCUMENTS

| 2,501,184 A | 3/1950 | Michaels ........................ 8/10 |
| 2,695,259 A | 11/1954 | Charle ........................ 167/88 |
| 3,697,643 A | * 10/1972 | Shepherd et al. .............. 424/63 |
| 3,914,403 A | * 10/1975 | Valan ........................... 424/47 |
| 4,423,031 A | * 12/1983 | Murui et al. .................. 424/63 |
| 4,559,057 A | 12/1985 | Bogaty et al. ................. 8/405 |
| 4,988,502 A | * 1/1991 | Ounanian et al. .............. 424/63 |
| 5,104,413 A | 4/1992 | Ikeda ........................... 8/405 |
| 5,297,566 A | * 3/1994 | Firstenberg et al. ......... 132/203 |
| 5,324,506 A | * 6/1994 | Calvo et al. .................. 424/63 |
| 5,460,808 A | * 10/1995 | Mausner .................... 424/70.7 |

FOREIGN PATENT DOCUMENTS

| AU | 7341374 | 3/1976 | ............ A61K/7/12 |
| JP | 49-2688 | 1/1974 | |

OTHER PUBLICATIONS

Remington's Pharmaceutical Sciences (15$^{th}$ Ed.), Osol et al. (Editors), Mack Publishing Co, Easton, PA., 1975, pp. 1646–1648 and 1656–1657.*
Chemical Abstracts 109(6):43304p, 1987, Teramoto.*
Chemical Abstracts 116(14):136012b, 1991, Filippenkov et al.*
Chemical Abstracts 113(12): 103205b, 1989, Mori et al.*
Chemical Abstracts 117(8): 76240h, 1991, He, W.*
Chemical Abstracts 111(14): 120606j, 1988, Kubota et al.*
Chemical Abstracts 111(14): 120605h, 1988, Kubota et al.*

* cited by examiner

Primary Examiner—Edward J. Webman
(74) Attorney, Agent, or Firm—O'Melveny & Meyers LLP

(57) ABSTRACT

A process for treating balding spots and a composition which when applied to areas of thinning or balding hair increases the width and visibility of the hairs within the thinning or balding area and thus obscures visibility of the scalp or skin underlying the hairs. A bonding agent helps make the spray more efficient in application, decreases undesirable overspray, and increases formula adherence to hair shafts.

19 Claims, No Drawings

BALDNESS COSMETIC AND METHOD OF APPLICATION

This application is a continuation application of Ser. No. 08/432,487, filed may 1, 1995, now abandoned which is a continuation application of Ser. No. 07/999,740, filed on Dec. 31, 1992, now abandoned.

BACKGROUND

1. Field of Invention

This invention relates to a cosmetic for obscuring balding areas by enhancing the visibility of existing hair within the balding area and a novel method of application.

2. Description Of Prior Art

Baldness has been a problem, both for men and women, throughout the ages. A thinning scalp has long been a traditional sign of aging.

People have used hair pieces, hair weaves, internal and externally applied medicines, hair transplant and scalp reduction surgeries, and many other means to try to avoid appearing bald. Some attempts have worked, but most have proven expensive, difficult and at best only partially successful.

SUMMART OF INVENTION

In order to understand how the present invention works in hiding baldness, it helps to understand what baldness is to begin with.

Male pattern baldness is in fact not generally a total elimination of all hair within a balding area, but instead a reduction of hair size, visibility and count within the balding area. Even an individual who has a clearly visible scalp generally has a substantial number of small hairs still left in the balding area. The problem is that the hairs that are left are too few, too translucent, and too small to visually cover the scalp.

Baldness in women generally differs from that found in men. Instead of hairs shrinking in size and losing pigmentation and mass, women typically suffer a reduction in hair count over part or all of their scalp. What women share in common with men, however, is that the areas where the skin or scalp show through the hair usually still have hair, but hair in insufficient numbers and sizes to obscure the underlying epidermis.

GENERAL DESCRIPTION

The present invention takes advantage of remaining hair within a balding area by enlarging its size and enhancing its visibility. Specifically, the present invention thickens and adds pigment to the existing hairs which in turn, increases their prominence and visibility and thus obscures the underlying scalp or skin.

Embodiments of the present invention work so well in fact, that both men and women who have clearly bald areas can cosmetically eliminate the areas in just a matter of several seconds.

In a previous invention (Australian Patent No. 73,413/74) Kenneth Pond disclosed a composition which is inferior to embodiments using the present invention.

Embodiments using aspects of our present invention may improve over embodiments using the previous invention in several areas. First, relative to the earlier first invention, embodiments using our present invention may create significantly less overspray (the airborne dust from an aerosol which is formed from aerosol agents which don't adhere to their target). Next, embodiments using our present invention may measurably decrease undesirable transfer of the baldness cosmetic onto clothing and other objects the hair may contact or come into proximity with. In addition, aspects of our present invention may noticeably soften the treated hair in and around the balding area both visually, and to the touch. Also, aspects of our present invention may make the hair look more natural by increasing its surface sheen. Finally, embodiments using our present invention may be resistant to being washed out in the rain or by heavy perspiration.

DETAILED DESCRIPTION

Embodiments using our present invention may have up to four parts including: a colored hair thickener, a finishing spray, a hair cleanser and a special hair softener.

Although all four above mentioned parts are not necessary to practice our present invention, the combination of the four parts produces very satisfactory results.

A typical use of such a preferred embodiment may start with washing the hair using the present invention's hair cleanser. The hair is first wetted and the cleanser poured out of its bottle onto the hand and applied to the hair in conventional shampooing fashion.

The hair cleanser of this embodiment may differ from many commercial shampoos in that it leaves little or no residue on the hair and underlying skin. This helps build static charge on the hair to attract the colored hair thickener. This is also intended to provide a clean surface to help the hair thickener and finishing spray, which will both be applied later, to better adhere to the hair and skin.

The hair cleanser also may contain strengthened detergents which will remove water resistant resins which may be used in the hair thickener and/or in the finishing spray. Such water resistant resins may be present to prevent an embodiment from washing out in the rain or under heavy perspiration.

After rinsing, drying and styling the hair in the normal manner, the colored hair thickener is applied from its aerosol can with the can nozzle held 3 to 6 inches from the balding area. This aerosol spray is applied directly on and around the hair and skin of the balding area. It is best to blend the application in the balding area with the surrounding hair for a more natural appearance.

The hair thickener sticks to each hair shaft, increasing its mass, visibility and skin obscuring ability. It also coats the underlying skin, preventing direct skin observation regardless of the sufficiency of hair coverage. Providing adequate hair is present in the balding area, the bald spot, after the application of hair thickener, generally appears to be mostly or completely eliminated.

After the hair thickener dries, the finishing spray may be applied from its aerosol can. Here the product is sprayed with the can nozzle held 8 to 12 inches from the area being sprayed, in a manner typical of applying a men's or women's hair styling spray.

The finishing spray helps adhere the hair thickener to the hair shafts and skin. With proper formulation, it also may help add sheen to the surface of the hairs coated with the thickener. Also with proper formulation, such as the addition of water resistant resins, it may help prevent the thickener from being washed out in the rain or by heavy perspiration.

Once the finishing spray has dried, the hair may be styled by lightly brushing its outer surface with a comb, or with a brush, such as an inexpensive coarse-toothed plastic styling brush. This is a light brushing which should not scrape the skin or scalp. Brushing the scalp can remove some or all of the hair thickener. This brushing besides moving the hair into place, may help soften the hair and blend the treated area with its surroundings.

Removal of the hair thickener and finishing spray from the hair may be accomplished by again using the hair cleanser in the manner described above, or through use of any of a variety of conventionally available shampoos. This removal can be done at any time during or after the application of the colored hair thickener and finishing shield.

It is important to note that there are many variations to the above procedure that may be practiced. As an example, it may not be necessary to use the hair cleanser prior to applying the hair thickener. Freshly washed hair is not even necessarily a requirement for an embodiment to work.

Embodiments of the hair thickener may be applied and used without using a finishing spray. The finishing spray generally reduces the amount of hair thickener which may transfer onto clothing and other objects but is not essential for an embodiment to work.

Another way to apply the hair thickener is to apply the finishing shield first, then apply the hair thickener before the finishing shield dries. This may then be followed, as an optional procedure, with another application of the finishing shield.

The special hair softener's use is also optional. If it is used, it is applied any time after the hair thickener and finishing shield have been applied. The hair is wetted under a shower for just a few seconds without hand agitation. The special hair softener is then applied to the outer surface of the hair, again with minimal hand agitation. A final short rinse under the shower removes most of the special hair softener, but leaves the hair very soft in both the areas treated and untreated with hair thickener.

One knowledgeable in the art will realize that there are many different formulations which can be used to practice the present invention. What follows is one exemplary embodiment of a formulation for the hair cleanser, hair thickener, finishing spray, and softener.

Formulation for Colored Hair Thickener in Black:

| INGREDIENT | WT/WT | MAX % | MIN % |
| --- | --- | --- | --- |
| SD Alcohol 40 ANHYDROUS (200 proof) | 13.84% | 30.00% | 5.00% |
| PVP/VA Copolymer | 2.36% | 6.00% | 1.00% |
| Talc | 0.41% | 1.00% | 0.10% |
| Iron Oxide Black | 4.10% | 8.00% | 1.00% |
| Iron Oxide Umber | 0.51% | 1.50% | 0.10% |
| Iron Oxide Ochre | .10% | 0.50% | 0.10% |
| Silica | 1.24% | 4.00% | 0.50% |
| Propellant (Isobutane/Propane) | 77.54% | 95.00% | 50.00% |
| TOTAL | 100.00% | | |

Formulation for Colored Hair Thickener in White:

| INGREDIENT | WT/WT | MAX % | MIN % |
| --- | --- | --- | --- |
| SD Alcohol 40 ANHYDROUS (200 proof) | 13.84% | 30.00% | 5.00% |
| PVP/VA Copolymer | 2.36% | 6.00% | 1.00% |
| Talc | 2.69% | 6.00% | 1.00% |
| Iron Oxide Black | 0.02% | 1.00% | 0.00% |
| Titanium Dioxide | 2.69% | 6.00% | 1.00% |
| Silica | 1.12% | 4.00% | 0.50% |
| Propellant (Isobutane/Propane) | 77.28% | 95.00% | 50.00% |
| TOTAL | 100.00% | | |

Manufacturing Procedures:

Disperse PVP/VA copolymer, talc, silica, titanium dioxide and iron oxide in SD alcohol until homogenous, fill into aerosol container and charge with propellant.

Distinctive Features:

The colored hair thickener described in this preferred embodiment contains a resin (PVP/VA Copolymer) which reduces overspray and helps bond the colored hair thickener to the hair and skin. This resin also helps increase the amount of hair thickening that the colored hair thickener can produce.

The alcohol is present to aid in filling the aerosol cans with a slurry mix. It may be replaced by any of a wide range of other volatile liquids such as isopentane, or acetone. It also may be eliminated altogether and the aerosol cans filled with a dry mix plus propellant. The pigments suggested may be replaced with any of a variety of pigments known in the art, to obtain particular colors.

Formulation for Finishing Shield:

| INGREDIENT | WT/WT |
| --- | --- |
| SD Alcohol 40-2, Anhydrous (200 proof) | 93.63% |
| Resyn 28-2930 (a VA/crotonates/vinyl neodecanoate copolymer) | 5.50% |
| AMP Regular (AMP 99%) (aminomethyl propanol) | 0.47% |
| 193 Fluid/Rhodosil 5193 (dimethicone copolyol) | 0.15% |
| DC 556 Silicone Fluid, Cosm. (phenyl trimethicone) | 0.10% |
| Dehyquart SP - quarternium - 52 | 0.05% |
| Fragrance | 0.10% |
| TOTAL | 100.00% |

Manufacturing Procedures:

To a portion of the SDA in a SS tank, add the resin with high speed dispersion.
Add AMP, continue dispersion until dissolved.
Add balance of ingredients with good agitation.
Mix for 30 minutes or until uniform.
Fill Ratio:  Concentrate  75%
            Propellant A-31  25%  (Isobutane/Propane)
                             100%

Distinctive Features:

The above finishing shield imparts a high degree of sheen to the hair due to a high content of silicone. This sheen is important in making the treated hair look natural. The colored hair thickener has a powder texture which imparts a matte appearance. Untreated hair by contrast has a natural sheen. The high amount of silicone helps restore sheen and luster to the areas treated with colored hair thickener.

Formulation for Hair Cleanser:

| INGREDIENT | WT/WT |
| --- | --- |
| Water, Deionized | 56.15% |
| AMP Regular (AMP 99%) (Aminomethyl Propanol) | 1.50% |
| Crothix (Polyol Alkoxyl Ester) | 1.00% |
| Stepanol WAT (Tea-Lauryl Sulfate) | 32.00% |
| Standamide KD (Cocamide DEA) | 5.00% |
| Tetrasodium EDTA (Grace HAMP_ENE Na1/Ciba-Geigy) | 0.10% |
| Actiplex 562 Al (Extracts of calendula, rosemary, chamomile and nettle) | 0.10% |
| Germall II (Diazolidinyl Urea) | 0.20% |
| Lexaine C (Cocamidopropyl Betaine) | 2.50% |
| Triton X-100 (Oxtoxynol-9) | 0.70% |
| Fragrance | 0.50% |
| Mint Green (FD&C Blue No. 1 and FD&C Yellow No. 5) | 0.00% |
| FD & C Blue #1 | 0.00% |
| H Kohnstamm FD&C Red #4 | 0.00% |
| Ammonium Chloride | 0.25% |
| TOTAL | 100.00% |

Distinctive Features:

One knowledgeable in the art will realize that the above hair cleanser leaves little or no residues on the hair and underlying skin, leaving both completely or close to completely clean. This helps in creating static change in the hair to attract the colored hair thickener. The cleanliness also helps the colored hair thickener and finishing spray adhere to the hair and skin once the thickener and finishing spray has been applied.

Such a knowledgeable person will also realize that the detergents in the above are strong enough to remove water resistant resins, such as PVP/VA Copolymer and resyn 28-2930, which may be used in making the hair thickener and/or the finishing spray.

Both the lack of residue causing agents and the use of detergents which are specifically directed to removing resins should be considered options, either or both of which may be absent from an embodiment practicing aspects of the present invention.

Formulation for Special Hair Softener:

| INGREDIENT | WT/WT |
| --- | --- |
| Special Blend of Cetearyl Alcohol, PEG-40 Hydrogenated Castor Oil, Stearalkonium Chloride | 6.00% |
| Dicetyldimonium Chloride | 1.00% |
| Fragrance | 0.05% |
| Diazolidinyl Urea | 0.10% |
| Dl Water | 92.85% |
| TOTAL | 100.00% |

Distinctive Features:

One knowledgeable in the art will recognize the above closely resembles formulations practice by conventional hair softeners. The distinctive feature of this embodiment component lies in the manner of its use, not in its composition and manufacture.

What have been described are certain aspects of a hair thickening spray which obscures bald or thinning hair areas. It is understood that the foregoing description and accompanying illustrations are merely exemplary and are in no way intended to limit the scope of the invention, which is defined solely by the appended claims and their equivalents. Various changes and modifications to the preferred embodiments will be apparent to those skilled in the art. Such changes and modifications may include, but are not limited to: applying the composition with means other than an aerosol container such as using a powder puff or salt shaker or perfume atomizer or pump dispenser or hand pump aerosol; changing the proportions of the constituent components of the composition, such as decreasing the Aerosil 200 to 1 gm or increasing the alcohol to 15 ml so cans may be filled with a slurry fill; substituting other components for the components in the composition, such as using other pigments than those specified; applying the composition to hair other than human hair, such as to pets or other animals; spraying the finishing spray on first and then applying the hair thickener, even possibly before the finishing spray has had a chance to dry; spraying on several applications of the first spray, possibly alternating each application with an application of the second spray (the finishing spray); using a lighter weight pigment such as very fine plastic powder or powder such as is used in toners used in plain paper copiers; applying an embodiment to increase the visibility or thickness of other body hair such as beards and eyebrows, using other methods to apply the hair cleanser such as a spray-on hair cleanser, using other methods to apply the finishing spray such as a pump spray or pump aerosol, applying the hair thickener in two parts such as a thickener part and a pigmented part, putting pigment in the finishing spray and using it to color the hair instead of the hair thickener etc. Such changes and modifications can be made without departing from the spirit and scope of the invention. Accordingly, it is intended that all such changes and modifications be covered by the appended claims and equivalents.

What is claimed is:

1. A method for cosmetically treating balding scalp areas comprising the steps of:

applying a colored hair thickener from an aerosol container directly onto hair and skin of a balding scalp area, said colored hair thickener comprising an admix of pigment, bonding resin from about 1% to about 6% by weight, talc, silica, and volatile vehicle, said bonding resin consisting essentially of PVPNA copolymer, said colored hair thickener thereby sticking to shafts of said hair to increase mass and visibility of said hair shafts and coating said skin to prevent direct skin observation; and styling hair in and around said balding scalp area in a desired manner without scraping the skin of said balding scalp area.

2. The method of claim 1, further comprising the step of applying said colored hair thickener to hair surrounding said balding scalp area.

3. The method of claim 1, wherein said bonding resin of said colore hair thickener is in an amount from about 2% to 3% by weight.

4. The method of claim 1, wherein said pigment comprises at least one of iron oxide and titanium dioxide.

5. The method of claim 1, wherein said colored hair thickener further comprises a volatile liquid selected from a group consisting of acetone, isopentane and SD alcohol.

6. The method of claim 1, wherein said applying step further comprises applying id colored hair thickener with said aerosol container held approximately three to six inches from said balding scalp area.

7. The method of claim 1, further comprising the step of washing said balding scalp area prior to said applying step.

8. The method of claim 1, further comprising the step of applying a finishing spray to said balding scalp area after said applying step.

9. A method for cosmetically treating balding scalp areas comprising the steps of:

applying a hair thickener directly onto hair and skin of a balding scalp area, said hair thickener comprising a homogeneous mixture of talc, silica, pigment and resin, said hair thickener thereby sticking to shafts of said hair to increase mass and visibility of said hair shafts and coating said skin to prevent direct skin observation; and styling hair in and around said balding scalp area in a desired manner.

10. The method of claim 9, wherein the applying step further comprises applying the hair thickener wherein the resin consists essentially of a PVP/VA copolymer.

11. The method of claim 9, wherein the applying step further comprises applying the hair thickener further comprising a dispersing fluid, and the talc, silica, pigment, and resin are dispersed in the dispersing fluid.

12. The method of claim 11, wherein the applying step further comprises applying the hair thickener further comprising a propellant.

13. The method of claim 12, wherein the applying step further comprises applying the hair thickener wherein the resin is in an amount of 1 % to 6%, by weight.

14. The method of claim 12, wherein the applying step further comprises applying the hair thickener wherein the silica is in an amount of 0.5% to 4%, by weight.

15. The method of claim 12, wherein the applying step further comprises applying the hair thickener wherein the talc is in an amount of 0.1% to 1%, by weight.

16. The method of claim 12, wherein the applying step further comprises applying the hair thickener wherein the talc is in an amount of 1 % to 6%, by weight.

17. The method of claim 12, wherein the applying step further comprises applying the hair thickener wherein the pigment is at least 1% of the colored hair thickener, by weight.

18. The method of claim 17, wherein the applying step further comprises applying the hair thickener wherein the pigment is less than 10% of the colored hair thickener, and wherein the resin is in an amount of 1 % to 6% by weight, the silica is in an amount of 0.5% to 4% by weight, and the talc is in an amount of 1% to 6% by weight.

19. The method of claim 17, wherein the applying step further comprises applying the hair thickener wherein the pigment is less than 10% of the colored hair thickener, and wherein the resin is in an amount of 1 % to 6% by weight, the silica is in an amount of 0.5% to 4% by weight, and the talc is in an amount of 0.1% to 1 % by weight.

* * * * *